(12) United States Patent
Munnerlyn et al.

(10) Patent No.: US 6,331,177 B1
(45) Date of Patent: Dec. 18, 2001

(54) MULTIPLE BEAM LASER SCULPTING SYSTEM AND METHOD

(75) Inventors: Audrey Munnerlyn, Mountain View; George Caudle, San Jose, both of CA (US)

(73) Assignee: VISX, Incorporated, Santa Clara, CA (US)

( * ) Notice: Subject to any disclaimer, the term of this patent is extended or adjusted under 35 U.S.C. 154(b) by 0 days.

(21) Appl. No.: 09/274,499

(22) Filed: Mar. 23, 1999

Related U.S. Application Data
(60) Provisional application No. 60/082,156, filed on Apr. 17, 1998.

(51) Int. Cl.⁷ .................................................. A61B 18/18
(52) U.S. Cl. ........................ 606/5; 219/121.69; 128/898
(58) Field of Search ................................... 606/2, 3, 4–6, 606/10–12; 219/121.6, 121.61, 121.64, 121.66, 121.69, 121.71, 121.72, 121.85; 128/898

(56) References Cited

U.S. PATENT DOCUMENTS

| | | |
|---|---|---|
| 4,547,037 | 10/1985 | Case . |
| 5,171,242 * | 12/1992 | Dewey et al. ............................ 606/4 |
| 5,336,216 * | 8/1994 | Dewey ...................................... 606/4 |
| 5,480,396 * | 1/1996 | Simon et al. . |
| 5,610,733 | 3/1997 | Feldman et al. . |
| 5,646,791 | 7/1997 | Glocker . |
| 5,683,379 | 11/1997 | Hohla . |
| 5,685,998 | 11/1997 | Shannon et al. . |
| 5,865,830 | 2/1999 | Parel et al. . |
| 5,921,981 | 7/1999 | Bahmanyar et al. . |
| 6,159,619 * | 12/2000 | Rockstroh et al. ................... 428/610 |

FOREIGN PATENT DOCUMENTS

WO 99/53992 * 10/1999 (WO) .

OTHER PUBLICATIONS

Krueger et al., "Diffractive smoothing of eximer laser ablation using a defocused beam" *Refractive & Corneal Surgery* (1994) 10:20–26.

Shimmick et al., "Axial and transverse displacement tolerances during excimer laser surgery for myopia" *SPIE* (1991) 1423:140–153.

Krueger et al "Diffractive smoothing of excimer laser ablation using a defocused beam", Refractive and Corneal Surgery (1994) 10:20–26.*

* cited by examiner

*Primary Examiner*—Michael Peffley
(74) *Attorney, Agent, or Firm*—Townsend and Townsend and Crew LLP

(57) ABSTRACT

The invention improves the laser sculpting of a region of a material to a predetermined shape by improving the smoothness and accuracy of surfaces formed by the sculpting technique. The technique includes projecting plurality of partially overlapping beams toward the region. The invention includes blurring an edge of an ablation to smooth an internal portion of the ablation that is separate from the edge. The blurred edge may be formed by the partially overlapping beams. Using a computer controlled laser delivery system, the position and shape of the overlapping beams may be precisely controlled to sculpt the material to a desired shape according to a laser treatment table.

14 Claims, 9 Drawing Sheets

MULTIPLE BEAM LASER SCULPTING SYSTEM AND METHOD

CROSS-REFERENCE TO RELATED APPLICATIONS

This application claims the benefit of priority from U.S. Provisional Patent Application Ser. No. 60/082,156, filed Apr. 17, 1998, the full disclosure of which is incorporated herein by reference.

BACKGROUND OF THE INVENTION

1. Field of the Invention

The present invention relates generally to systems and methods for sculpting materials, and more particularly to a laser ablation system and method for sculpting a lens in a cornea.

Lasers have been used for several years to sculpt materials into very precise shapes. Excimer lasers are now widely used to ablate tissue in a variety of surgical procedures, particularly for corneal ablation during refractive surgery. The exposure of the tissue is typically controlled to produce a desired change in corneal shape. The change in corneal shape may be intended to correct a refractive error of the eye so as to eliminate the need for corrective eyeglasses, or may be intended to remove a pathology from the eye.

Known laser eye procedures generally employ an ultraviolet or infrared laser to remove a microscopic layer of stromal tissue from the cornea of the eye to alter its refractive power. The laser removes a selected portion of the corneal tissue, often to correct refractive errors of the eye. Laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Selective photoablation of corneal tissues benefits from precise control over a laser beam. Control over the distribution of the ablative laser energy across the cornea may be provided by a variety of systems and methods, including the use of ablatable masks, moveable apertures, scanning systems that move laser beams of varying cross-section across the cornea, and the like. These laser control systems generally vary the profile of the laser beam, and thus the ablation area on which the laser impinges on the eye. As the ablation depth generally varies with the amount of laser energy, the distribution of laser energy across the laser beam is often kept as uniform as possible. The goal of this uniform energy distribution is to remove the corneal tissues uniformly throughout the laser cross-section. As excimer lasers produce laser beams as a series of laser pulses, the total ablation is often calculated as a series of ablations of uniform depth.

For laser refractive surgery to have an optimal result, the sculpting process should accurately remove corneal tissues so as to change the refractive characteristics of the eye in the desired manner. The tissues targeted for removal will generally be lens-shaped, and this lens-shaped ablation should often be surrounded by a smoothly tapering transition zone. Such a total ablation can only be approximated by the series of pulse ablations produced with most pulsed excimer lasers. This can result in ablations having undesirably abrupt changes in depth and/or staggered edges.

Several techniques have been proposed to smooth ablations. One proposal is to smooth the sharp edge of an ablation formed from an imaged aperture by defocusing the laser beam. An alternate proposal is to move the laser beam across the corneal surface between pulses so that the sequential pulses only partially overlap. Although refractive laser surgery using such approaches might be effective, the final ablations can often be less smooth than is desired. Known methods for defocusing of the laser beam may also reduce the accuracy of the overall refractive correction. Although partially overlapping sequential laser pulses can prevent the ablation edges of separate pulses from lining up, the size of each pulse edge is unaffected. Additionally, work in connection with the present invention has found that the precise shape of the actual ablation produced by a uniform laser pulse generally differs somewhat from the uniform ablation depth that has been theoretically predicted. Hence, the total ablation region can differ significantly from even the approximate lens shape that is intended.

In light of the above, it would be desirable to provide improved laser systems and methods for sculpting with lasers. It would be particularly desirable to provide new techniques for smoothing the ablations produced by lasers, especially the corneal ablations of laser refractive surgery. It would further be desirable if these improved techniques minimized unintended variations in the ablation depth, and did not significantly add to the cost or complexity of the laser systems.

2. Description of the Background Art

The following references are herein incorporated by reference in their entirety: U.S. Pat. No. 5,646,791 for "METHOD AND APPARATUS FOR TEMPORAL AND SPATIAL BEAM INTEGRATION;" U.S. Pat. No. 5,683,379 for "APPARATUS FOR MODIFYING THE SURFACE OF THE EYE THROUGH LARGE BEAM LASER POLISHING AND METHOD OF CONTROLLING THE APPARATUS;" U.S. Pat. No. 5,610,733 for "BEAM-HOMOGENIZER;" U.S. Pat. No. 4,547,037 for "HOLOGRAPHIC METHOD FOR PRODUCING DESIRED WAVEFRONT TRANSFORMATIONS;" U.S. Pat. No. 5,685,998 for "METHOD OF MINIMIZING DIFFRACTION GROOVE FORMATION ON LASER ETCHED SURFACES;" and U.S. patent application Ser. No. 08/968,380, for "METHOD AND SYSTEM FOR LASER TREATMENT OF REFRACTIVE ERRORS USING OFFSET IMAGING," as filed Nov. 12, 1998.

The publication "DIFFRACTIVE SMOOTHING OF EXCIMER LASER ABLATION USING A DEFOCUSED BEAM" by McDonnel et al., published in Refractive and Corneal Surgery, Volume 10 (January/February 1994) describes a technique for smoothing ablations and is herein incorporated by reference in its entirety. An article entitled "AXIAL AND TRANSVERSE DISPLACEMENT TOLERANCES DURING EXCIMER LASER SURGERY FOR MYOPIA" by Shimmick et al., SPIE Ophthalmic Technologies, Volume 1423, page 140 (1991) may be relevant, and is also incorporated herein by reference.

SUMMARY OF THE INVENTION

The present invention generally provides improved systems and methods for sculpting a material to effect a predetermined change in shape by ablating a region of the material. The techniques of the present invention generally improve the smoothness and accuracy of the ablated shape by directing a plurality of laser beams toward the targeted region so that the beams strike differing areas of the material. The beams will generally be produced by separating a single laser beam, the single beam comprising a series of laser pulses. The ablation areas may partially overlap during at least some portion of the ablation procedure, and/or they may be separated during at least some portion of the procedure. Regardless, the edge depth for each pulse at these areas can be significantly less than that of a pulse directed at a single ablation area, as might be produced by the unseparated beam. The methods and systems of the present invention manipulate the multiple beams so as to alter the ablation pattern formed from the differing beam areas, thereby allowing more accurate removal of a smooth region from the material, particularly when removing a lens-shaped region of corneal tissue using a pulsed laser.

The present invention also makes use of blurred ablation edges. Surprisingly, work in connection with the present invention has found that these blurred edges can be used to smooth the ablation at a significant distance from the edge. More specifically, known techniques for ablating materials typically create small irregularities or unintended features in the interior of the ablation. The blurred edges will often be produced by imaging an aperture with an imaging system arranged so that the surface of the eye (or other target material) is beyond the imaging system's depth of field. This can minimize the internal irregularities both at the microscopic level, as can be detected by optical interferometry, and at the macroscopic level, as can be detected by unaided human vision.

In a first aspect, the present invention provides a method for sculpting a material to effect a predetermined change in shape. The method comprises simultaneously directing a plurality of beams of ablative energy toward the material while the beams are directed at differing areas. As a result, the beams ablate a pattern from the material. The beams are manipulated so as to modify the ablation pattern. The ablative energy is then simultaneously directed along the manipulated beams.

In another aspect, the present invention provides a method for sculpting a material to effect a predetermined change in shape. The method comprises simultaneously directing ablative energy toward the material along a plurality of beams, each beam impacting at an associated ablation area of the material. The ablation areas only partially overlap, ideally so that a significant portion of the ablations extend beyond each other.

In another aspect, the invention includes a method for sculpting a material to effect a predetermined change in shape. The method comprises radiating a beam of ablative energy. A region of the material absorbs the ablative energy and ablates, the ablation having an edge. The ablation is shaped at a distance from the edge by blurring the edge.

The shaping of the ablation may include smoothing the ablation. Surprisingly, blurring the edge can smooth an internal portion of the ablation that is surrounded by, but separated from, the blurred edge. Preferably, a laser lases to create pulses of the ablative energy. The beam is formed from these pulses, and may be profiled with an aperture. An image of the aperture may be projected toward the material with an imaging system, and the edge may be blurred by positioning the material away from the depth of field of the imaging system. The blurring may be controlled by a collimating lens, and the imaging system may focus the beam to a waist near the back focal point of the imaging system.

In another aspect, the present invention provides a method for sculpting a lens in a region of a cornea of an eye. The method includes radiating a beam of an ablative energy by lasing a laser to produce a laser beam of the ablative energy. The beam comprises a multiplicity of laser beam pulses, and the energy is absorbed within a region of the cornea so as to ablate the region. The ablation has an edge, and an internal portion of the ablation can be smoothed by blurring the edge from a single pulse, the internal portion being surrounded by and separate from the blurred edge.

The present invention also provides a laser system for sculpting a region of a cornea to effect a predetermined change in shape. The system comprises at least one laser for generating a plurality of laser beams suitable for ablation of the cornea. An optical train is optically coupled to the beams so as to direct the plurality of optical beams toward differing areas of the cornea. The differing areas define an ablation pattern, and the optical train includes an adjustment mechanism for altering the ablation pattern.

In a further aspect, the invention provides a laser system for sculpting a region of a cornea to effect a predetermined change in shape. The system comprises a laser for generating a first beam of laser energy suitable for ablation of the cornea. An optical train is coupled to the first beam, the optical train including an optical element which separates the first beam into a plurality of laser beams. The optical train directs the plurality of optical beams toward partially overlapping areas of the cornea.

Therefore, it is an object of the invention to sculpt a material to effect a predetermined change in shape by partially overlapping a plurality of simultaneous laser beams. It is a further object of the invention to smooth an internal portion of an ablation that is not part of an edge of the ablation by blurring an edge of the ablation.

DESCRIPTION OF THE SPECIFIC EMBODIMENTS

The present invention is generally directed to structures, systems, and methods for sculpting materials by ablation. The techniques of the present invention generally improve the smoothness and control of laser sculpting of materials to a predetermined shape.

The techniques of the present invention are particularly well adapted for sculpting an exposed surface of the cornea of a human eye to effect a desired change in the patient's eyeglass prescription. A laser beam is typically sequentially pulsed to produce a time varying sequence of laser beam pulses. The laser beam pulses are scanned over a laser treatment area. The treatment area is exposed to a succession of individual pulses of the laser beam. The ablations within the treatment area are shaped and positioned so as to remove a predetermined geometry from the treatment area. Hence, the present invention will have benefits for photorefractive keratectomy (PRK including procedures to correct hyperopia, myopia, astigmatism, or any combination thereof), phototherapeutic keratectomy (PTK), laser in situ keratomileusis (LASIK), and the like.

As used herein, the term "beam" encompasses both pulses of laser light (or other radiant energy), and also the theoretical pulse path between pulses.

Figure 1:
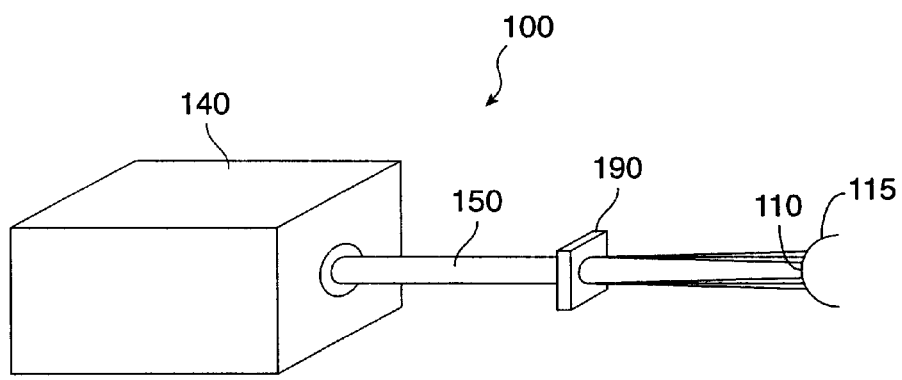
FIG. 1 is a schematic illustration of a laser system incorporating the principles of the present invention.

Turning now to the figures, FIG. 1 depicts a laser system 100 incorporating the present invention. A laser 140 emits a laser beam 150 which is preferably a 193 nm beam from an Argon Fluoride excimer laser. The laser beam 150 sculpts a region 110 of a material 115.

Figure 2:
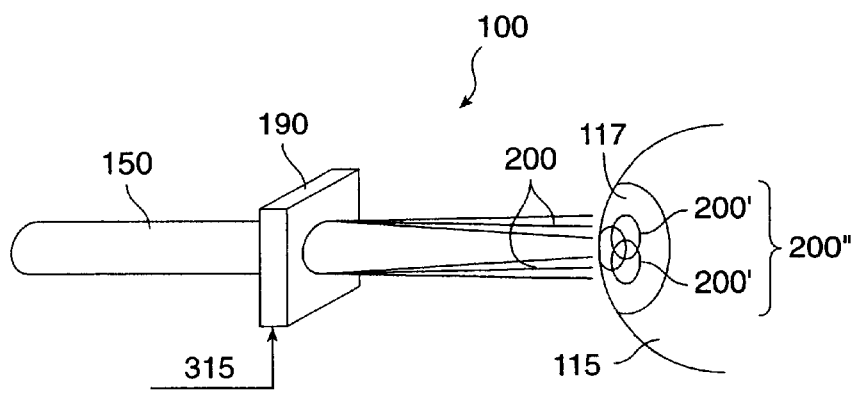
FIG. 2 schematically illustrates an optical element separating a first laser beam into a plurality of beams.

As can be seen more clearly in FIG. 2, the laser beam 150 may be separated into a plurality of laser beams 200 by an optical element 190. The beams 200 each ablate an associated area 200', the combined beam areas defining a pattern 200". The laser system manipulates this pattern to ablate a region or treatment area 117 of material 115 so as to selectively remove the region, typically to effect a predetermined change in refractive configuration of the material. To manipulate pattern, optical element 190 can be variably controlled by a signal from drive-line 315.

Figure 3:
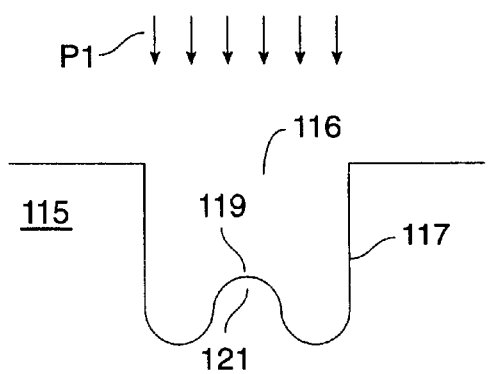
FIG. 3 schematically illustrates an ablation region which can be produced from a single laser beam with an aperture that is imaged in-focus on the targeted material.

As shown in FIG. 3, an ablation 116 formed in material 115 by a single uniform laser pulse P1 (or by a plurality of fully overlapping uniform pulses) may have certain undesirable features. An edge 117 of uniform beam ablation beam 116 may be steeper and deeper than is desirable, making it more difficult to combine a series of such uniform ablations into a smoothly contoured lens-shaped region. Additionally, an internal portion 119 of uniform ablation 116 may demonstrate an irregularity 121, the irregularity often including a relatively shallow ablated zone sometimes referred to as a central island. Additional irregularities may also include a series of petal-like variations in the ablation depth aligned around the ablation center at a distance from the ablation wall. These petals may be aligned with corners or discontinuities in an aperture or other structure defining the cross section of the laser beam.

Figure 4:
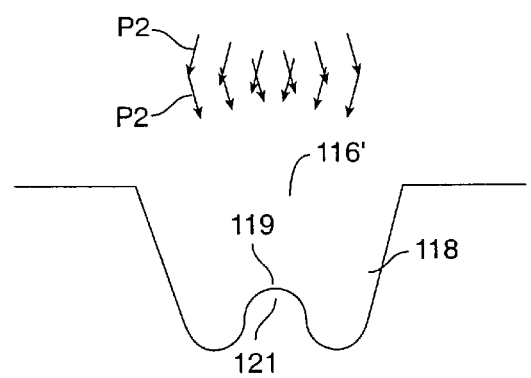
FIG. 4 schematically illustrates an ablation region which can be produced with a plurality of separated laser beams simultaneously directed at the targeted material using an imaging system that images an aperture at a significant distance from the material surface.

As shown in FIG. 4, smoothed ablation 116' may be made with a blurred or tapered ablation edge 118 surrounding central portion 119. Surprisingly, the size of irregularity 121 within central portion 119 may be decreased by the blurred ablation edge 118, even though central portion 119 is separate from the edge 118. The shape of the ablation adjacent edge 118 may further be controlled by directing a plurality of simultaneous laser pulses P2 onto slightly differing areas of the material, as will be explained in more detail hereinbelow.

As described above, the laser systems of the present invention will often include an optical element which separates a single laser beam (and hence its laser pulses) into a plurality of simultaneous beams (occurring with a single laser pulse). The optical train directs these beams toward differing areas of the targeted region, which differing areas may partially overlap, or may be entirely separate. Where each of the multiple beams typically has a cross-section similar to that of the single beam, the edge depth of the ablation areas from each pulse of the beams will be a fraction of the edge depth that would be produced by the single beam. Thus, the optical train of the laser system can modify and/or move the ablation pattern produced by the multiple beams to more accurately remove a targeted region with a shape having an arbitrarily curving surface.

Figure 7:
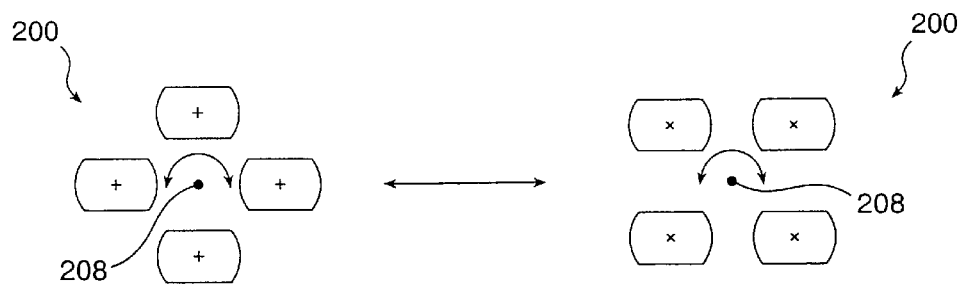
FIG. 7 schematically illustrates varying the ablation pattern by rotating the beams about a pattern center.
Figure 8:
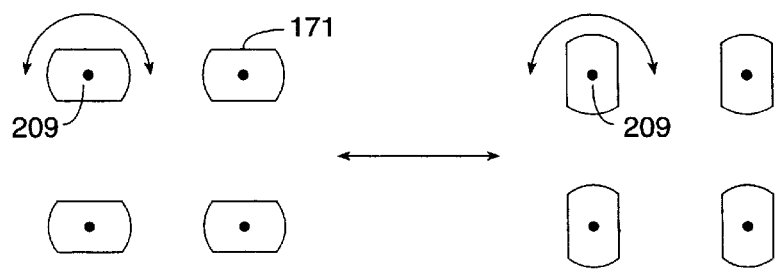
FIG. 8 schematically illustrates varying the ablation pattern by rotating the beams about differing axes.
Figure 9:
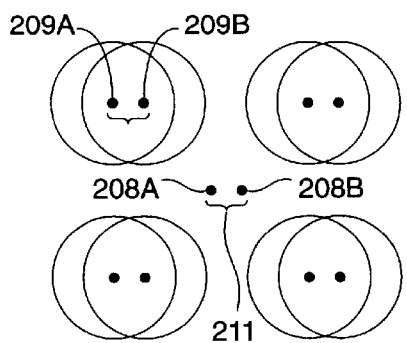
FIG. 9 schematically illustrates translation of the pattern relative to the material, as will again typically occur at least partially between pulses.
Figure 10:
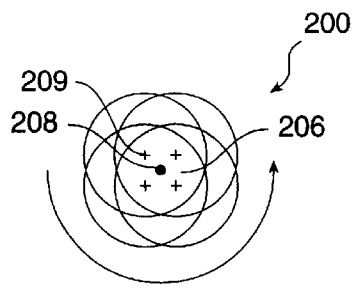
FIG. 10 schematically illustrates rotation of a pattern defined by four separated laser beams about a pattern center, wherein the ablation areas of the four beams partially overlap so that a central portion is ablated by all the beams, while a peripheral area is ablated by fewer beams so as to define a tapering transition.
Figure 11:
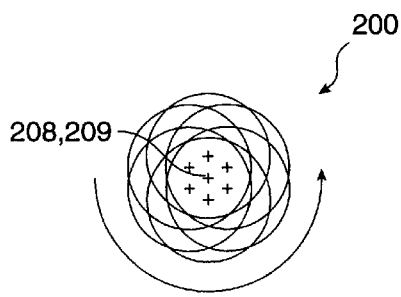
FIG. 11 schematically illustrates rotation of a pattern defined by seven partially overlapping laser beams about a pattern center.

FIGS. 5 through 8 generally illustrate modifications to the ablation patterns produced with multiple laser beams, while FIGS. 9 through 11 illustrate movements of the pattern across the material. First describing modifications to the ablation patterns, each ablation area has a size, a shape, and a center. The optical train of the laser will often manipulate the first beam and/or the individual beams so as to alter at least one pattern characteristic or dimension such as the size of at least some of the ablation areas, the shape of at least some of the ablation areas, and a distance between at least some of the ablation area centers. This change will often occur at least partially between pulses of the laser, preferably occurring substantially entirely between pulses.

Figure 5:
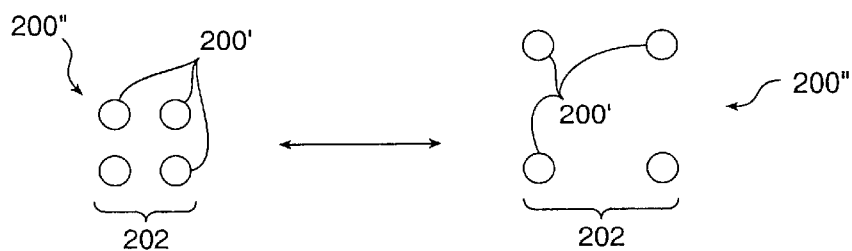
FIG. 5 schematically illustrates varying an ablation pattern by changing a separation distance between separated ablation areas produced by multiple simultaneous laser beams, as will typically occur at least partially between the pulses of a pulsed laser beam.
Figure 6:
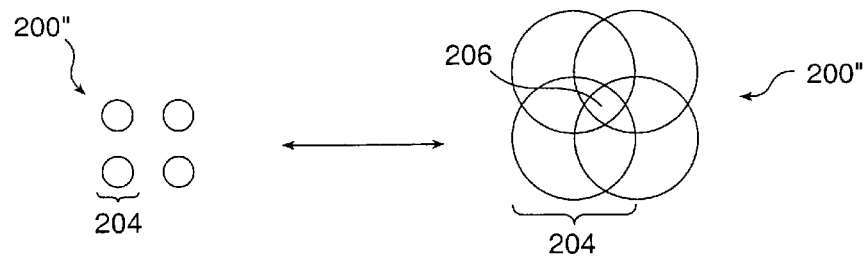
FIG. 6 schematically illustrates varying the ablation pattern by changing the size of the separated laser beams.

Referring now to FIG. 5, one variation of ablation pattern 200" comprises a change in the separation 202 between ablation areas 200'. As depicted in the figure, the separation 202 between the plurality of simultaneous pulses 200 may be increased or decreased. Additionally, a dimension of the cross-sectional size 204 of the simultaneous beams may be varied as shown in FIG. 6. As shown in the figure, the size may be increased or decreased.

An increase of size 204 may cause the beams to overlap and create a region of overlapping beams 206. The size of this overlapping region may be controlled by varying size 204 of the simultaneous beams, the spacing between beams, the beam shapes and/or rotational orientation within the pattern, and the like. The plurality of simultaneous beams 200 may be rotated about a common center of rotation 208 amid the pulses of laser 140 as shown in FIG. 7. Additionally, the simultaneous beams of plurality 200 may be rotated about other centers of rotation. For example, one of the ablation areas may be rotated about a center of rotation within that ablation area, as shown in FIG. 8.

Movement of the overall ablation pattern may also be used to sculpt smooth shapes from the target material. The pattern generally has a pattern center, and the predetermined change in shape will often define a sculpting center, such as the ocular axis of the eye. Movements of the pattern may include moving the pattern over the material by translating the pattern center relative to the sculpting center, and/or rotating the pattern about the pattern center (or some other arbitrary axis. Translation 211 of the beams is shown in FIG. 9.

Figure 12:
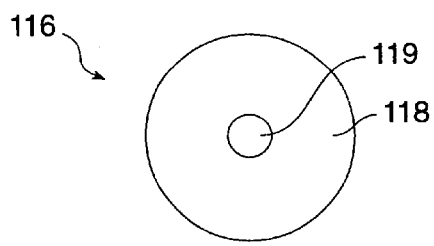
FIG. 12 schematically illustrates partially overlapping a plurality of beams and rotating the pattern so that the internal portion is about 10% of the total ablation.
Figure 13:
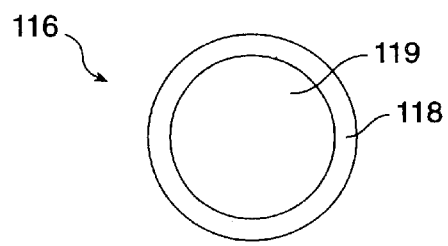
FIG. 13 schematically illustrates partially overlapping a plurality of beams and rotating the pattern so that the internal portion of the ablation is about 90% of the total ablation.

As shown in FIGS. 10 and 11, rotating an ablation pattern defined by partially overlapping ablation areas about a common center 208 can help produce a smoothly tapering transition zone about the region sculpted by overlapping beams 206. This provides an additional mechanism for producing blurred edge 118. The relative size of the blurred ablation edge 118 to the internal portion 119 of ablation 116 may be controlled. For example, the internal portion 119 may be as small as about 10% of the ablation 116 as shown in FIG. 12. Alternatively, internal portion 119 may occupy 90% of ablation 116 as shown in FIG. 13. Interestingly, a diffractive optic might also be used to produce similar ablation regions from each laser pulse.

Figure 14:
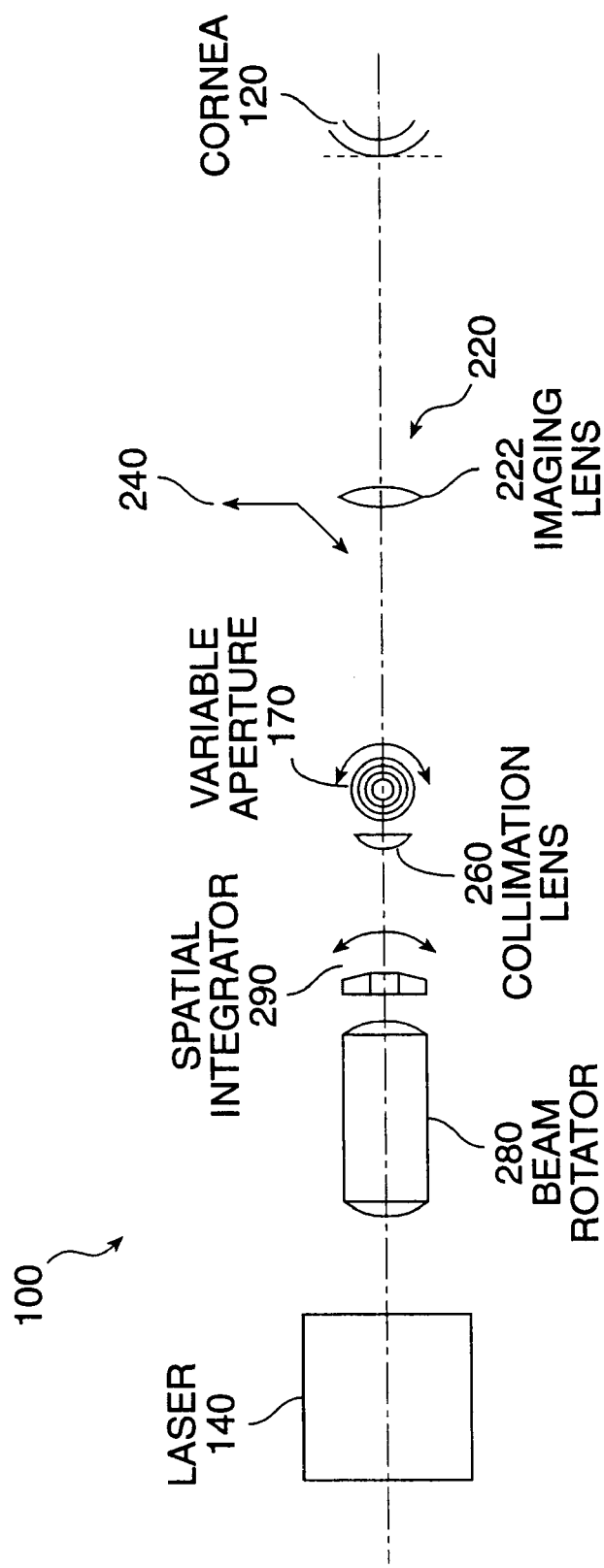
FIG. 14 schematically illustrates a laser delivery system for incorporating the invention.

A wide variety of laser system structures might be used to practice the smoothed ablation methods of the present invention. An exemplary embodiment comprises many of the elements of a VISX Star Excimer Laser System, available from VISX INCORPORATED of Santa Clara, Calif. For example, the optical elements of laser system 100 shown in FIG. 14 may incorporate the present invention. Laser 140 pulses to produce laser beam 150. Laser beam 150 is rotated by beam rotator 280. Laser beam 150 and spatial integrator 290 preferably rotate at twice the rotation rate of beam rotator 280. This rotation of spatial integrator 290 and laser beam 150 rotates the simultaneous plurality of laser beams 200 about a common center 208 as shown in FIG. 7. Several of these elements are described in more detail in U.S. Pat. No. 5,646,791, and in U.S. patent application Ser. No. 08/968,380.

Figure 15:
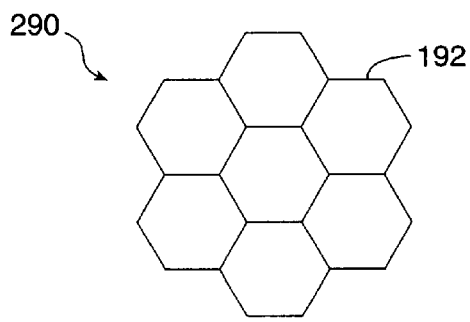
FIGS. 15 and 15A schematically illustrates a beam separating optical element comprising a hexagonal array for separating a first laser beam into a plurality of laser beams in the laser delivery system of FIG. 14.
Figure 15A:
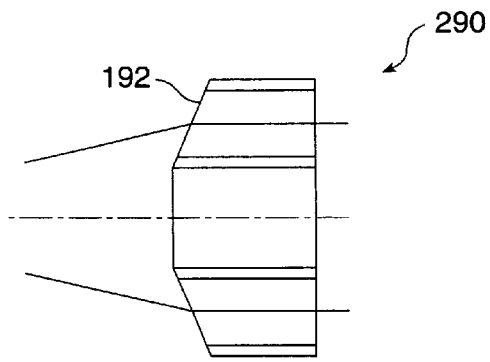
Figure 16:
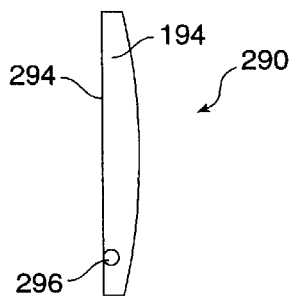
FIGS. 16 and 16A schematically illustrate an alternative beam separating optical element comprising a diffractive optic for separating the first laser beam into several laser beams.
Figure 16A:
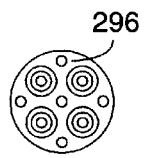

Advantageously, optical elements which have previously found use as spatial integrators may be used to separate laser beam 150 into a plurality of simultaneous beams 200. For example, FIGS. 15 and 15A schematically illustrate a hexagonal array of prisms 192 that may positioned to intercept laser beam 150. Alternatively, a diffractive array spatial integrator 194, as shown in FIGS. 16 and 16A, may be used.

Figure 17:
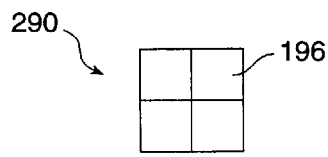
FIG. 17 schematically illustrates a beam separating optical element comprising a rectangular array for separating a laser beam into four laser beams.

The diffractive array spatial integrator contains a repeating array of phase shifting elements 296 on diffractive surface 294. As a still further alternative, a rectangular array spatial integrator 196 may used, as shown in FIG. 17.

The number of beams formed by a spatial integrator may be determined by the elements of the spatial integrator. For example, rectangular array 196 may produce four partially overlapping beams as shown in FIG. 10. By rotating the integrator 196, the beams will rotate about a common center 208. Alternatively, a 7 element hexagonal array integrator 192 may produce seven overlapping simultaneous beams as shown in FIG. 11. The laser beam intensity of the simultaneous beams may vary as the spatial integrator 290 rotates.

Figure 18:
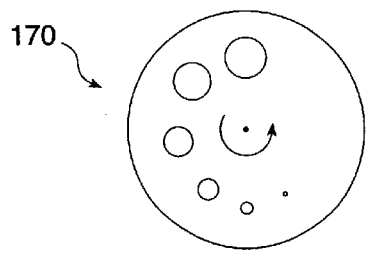
FIG. 18 schematically illustrates a variable aperture comprising an aperture wheel for selectively varying the size of the separated laser beams.
Figure 19:
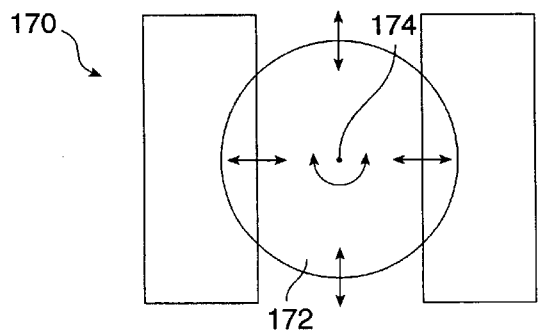
FIG. 19 schematically illustrates a variable aperture comprising a variable width slot and a variable iris for use in the laser delivery system of FIG. 14.

As can be understood with reference to FIGS. 7, 8, 18, and 19, a variable aperture 170 may be used to profile the single laser beam and/or the plurality of laser beams so as to change the size and shape of each beam of the pattern, or of the pattern overall. By intercepting the plurality of laser beams 200 with variable aperture 170, the overall size and shape of the ablation pattern may be controlled. For example an aperture wheel may be selectively rotated to pass only a portion of the simultaneous beams, thereby varying the size of the passed portion, as shown in FIG. 18. Alternatively, a variable slot 172 may selectively pass a portion of the first beam, thereby allowing the slot to change the shape of each of the plurality of beams that are generated therefrom. Variable slot 172 is preferably rotatable about center of rotation 174 and may be selectively varied in both length and width. The variable slot may be combined with a variable iris or the like to offer additional control over the ablation areas that define the ablation pattern.

Figure 20:
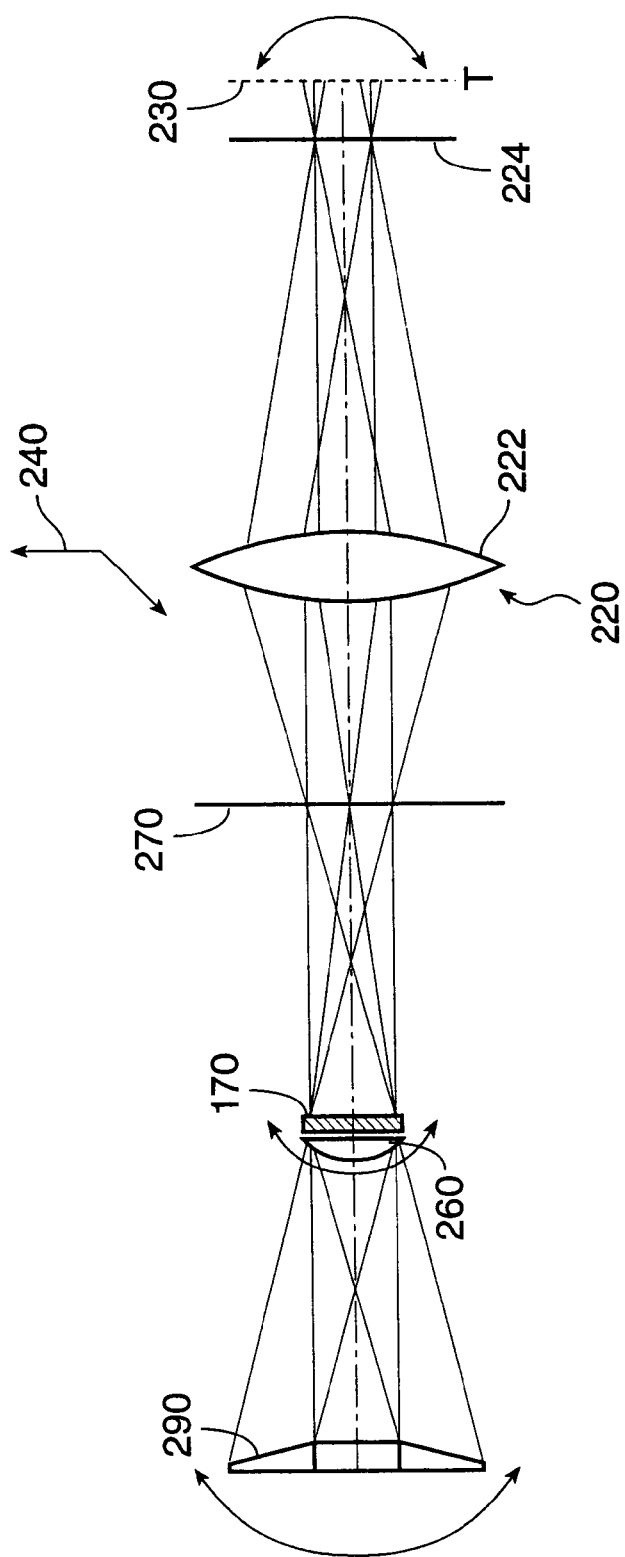
FIG. 20 schematically illustrates an imaging system for imaging an aperture toward and at a distance from the target material so that an image of the aperture is controllably blurred on the target material.

The present invention also provides a system for imaging an aperture toward the target material so that an edge of the resulting ablation will be blurred. As illustrated in FIG. 20, a simultaneous plurality of beams can rotate as they pass through a collimation lens 260 and a variable aperture 170. By rotating variable aperture 170, the simultaneous plurality of laser beams 200 may rotate about differing centers of rotation, such as rotation center 209 of FIG. 8. Collimation lens 260 focuses the plurality of simultaneous beams to a waist 270 near a focal point of an imaging system 220, the imaging system including an imaging lens 222. Imaging lens 222 projects a focused image 224 of the variable aperture 170 at a distance from cornea 120 and outside the depth of field of system 220. As a result, the image of the aperture formed on the cornea (when the cornea is disposed at target plane T) is blurred, thereby producing a blurred ablation edge.

Advantageously, the blurred image 230 formed on cornea 120 includes the plurality of simultaneous partially overlapping beams 200. Even though the image 224 of aperture 170 may be considered blurred, the individual beams of the plurality 200 may still appear focused on cornea 120 and exhibit an aperture structure 171 of aperture 170 when the plurality is separated and partially overlapping. A scanning element 240 such as a translating imaging lens 222 preferably translates the separated plurality of simultaneous beams 200 over the treatment area 117 of cornea 120. If desired, alternate embodiments of scanning element 240 such as moving prisms and mirrors may be used to translate the plurality of simultaneous beams 200 over treatment area 117 of cornea 200.

Figure 21:
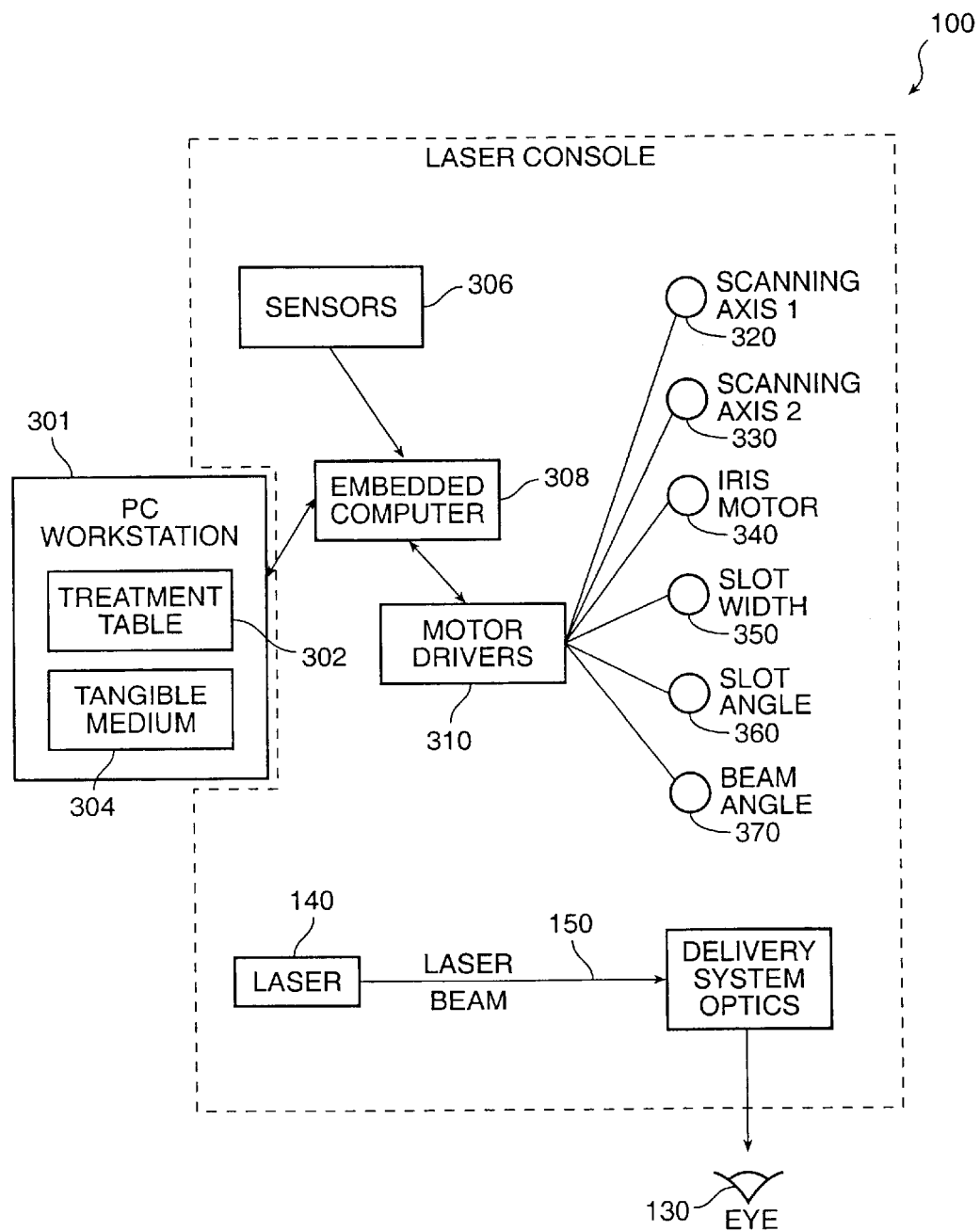
FIG. 21 schematically illustrates a computer control system for ablating a surface to the shape specified in a laser treatment table.

In a further aspect of an exemplary embodiment including elements of a VISX STAR Excimer Laser system, a computer control system enables precise control of the laser system 100 to sculpt a surface to a shape specified in a laser treatment table 302, as shown in FIG. 21. A PC workstation 301 receives instruction from a computer program stored on tangible medium 304 to generate a treatment table 302. An embedded computer 308 within the laser system 100 is in electronic communication with PC workstation 301.

In an alternate embodiment, a PC workstation may be embedded in laser system 100 and function as both embedded computer 308 and PC workstation 301. Embedded computer 308 is in electronic communication with a plurality of sensors 306 and a plurality of motor drivers 310.

Motor drivers coupled to the computer control the position of various elements of laser system 100 according to treatment table 302. For example, first and second scanning axes 320 and 330 preferably control the position of scanning element 240 and translation of the plurality of simultaneous beams 200 over treatment area 117. Further, iris motor 340 controls the length of variable slot 172, and slot width driver 350 controls the width of variable slot 172. Slot angle driver 360 controls the rotation of variable slot 172 about axis 174, and beam angle driver 370 controls the rotation of beam rotator 280, beam 150 and spatial integrator 290. Laser 140 is pulsed to generate laser beam 150 after the various elements of system 100 have been positioned to create a desired ablation on eye 130.

A further embodiment of the invention may be incorporated in existing laser systems. A further exemplary embodiment of the invention may be retrofitted into the VISX Star Excimer Laser System. By sliding variable slot 172 a distance of 11 mm toward laser 140 and lowering treatment area 117 a distance of 3 mm from imaging lens 222, the VISX Star Excimer Laser System can ablate improved shapes with a plurality of separated simultaneous laser beams when controlled by a modified computer program, according to the principles of the present invention.

Figure 22:
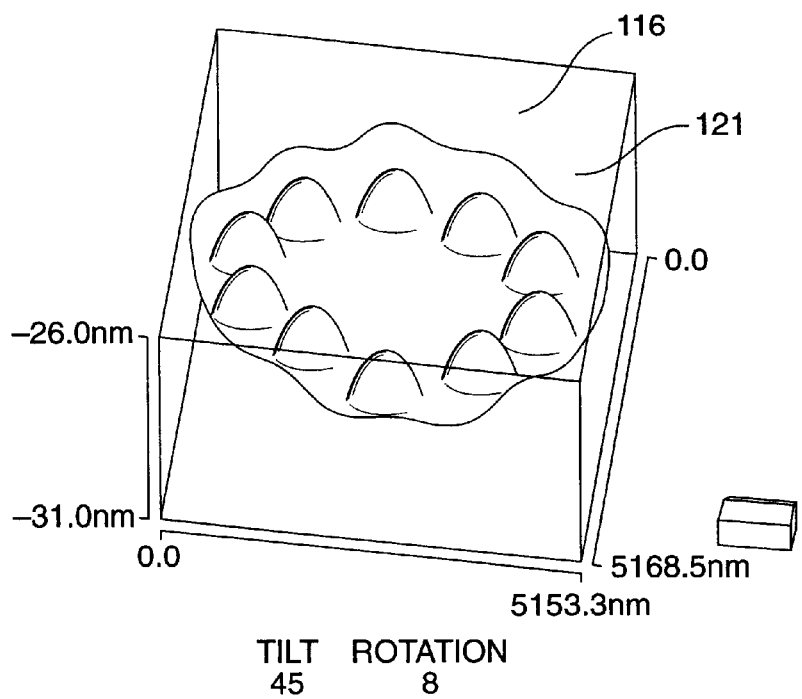
FIG. 22 illustrates an ablation made with a prior art laser system.
Figure 23:
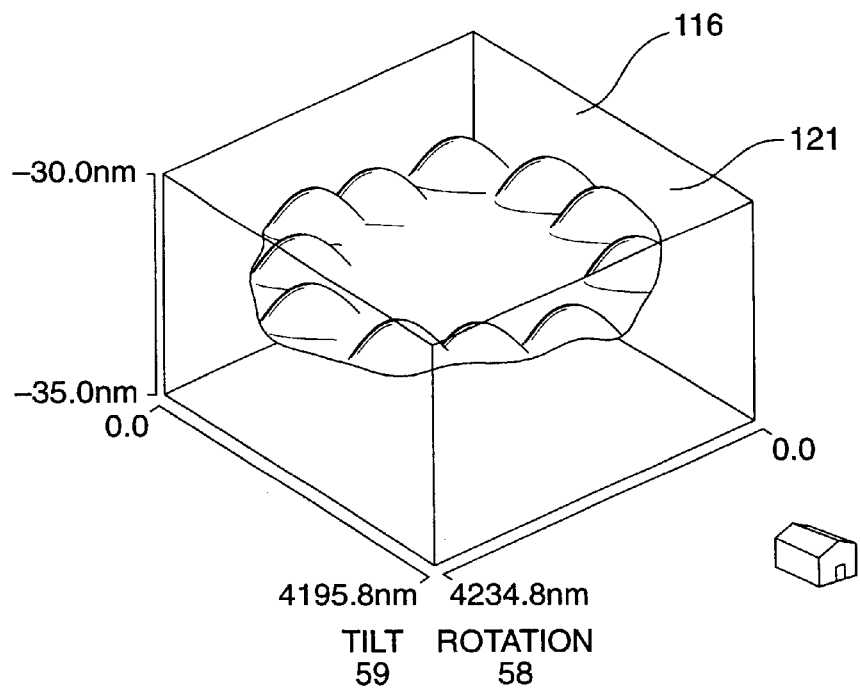
FIG. 23 illustrates an ablation made with the laser system of the present invention.

Experimentally, the invention has demonstrated improved ablations in materials such as plastic. For example, FIG. 22 illustrates a measurement of an ablation contour made with a laser. FIG. 23 illustrates a measurement of an ablation made with a laser incorporating the invention. An irregularity 121 of ablation 116 may be seen in the prior art ablation shown in FIG. 22, and irregularity 121 is reduced in size in ablation 116 incorporating the invention as shown in FIG. 23. More specifically, the height of the petal-like structures produced during a standard flat ablation may be reduced by 40% or more, from a range of about 0.7 mm to 1.4 mm to a range of about 0.4 mm to 0.8 mm. It should be noted that these numbers, and the ablations of FIGS. 22 and 23, are merely representative of the advantages provided by one portion of the present invention. These ablations were actually produced using fixed laser beams from laser systems having differing numbers of iris leaves.

While the above provides a full and complete disclosure of the preferred embodiments to the invention, various modifications, alternate constructions and equivalents may be employed as desired. For example, lasers of other appropriate wavelengths other than laser 140 may be used, if desired and effective. Also, energy beam systems that work on other ablation principals such ultrasonic and thermal ablation may be used to implement the invention. Therefore, the above description and illustrations should not be construed as limiting the invention, which is defined solely by the appended claims.

What is claimed is:

1. A method for sculpting a material to effect a predetermined change in shape, the method comprising:

radiating a beam of an ablative energy;

absorbing the energy within a region of the material so as to ablate the region, the ablation having an edge; and, shaping the ablation at a distance from the edge by blurring the edge.

2. The method of claim 1, wherein the step of shaping further comprises smoothing the ablation.

3. The method of claim 2, wherein the smoothing step smoothes an internal portion of the ablation, the internal portion being surrounded by and separated from the blurred edge.

4. The method of claim 1, wherein the step of radiating further comprises lasing a laser to produce the beam of ablative energy, the beam comprising a plurality of laser pulses.

5. The method of claim 4, further comprising intercepting the beam with an aperture.

6. The method of claim 5, further comprising projecting an image of the aperture toward the region with an imaging system.

7. The method of claim 6, wherein the imaging step comprises projecting a focused image of the aperture at a distance from the surface and beyond a depth of field of the imaging system.

8. The method of claim 6, further comprising collimating the laser beam near the material by focusing the beam to a waist near a focal point of the imaging system.

9. The method of claim 1, further comprising partially overlapping a plurality of simultaneous laser beams on the region, the beams being directed along a plurality of beam paths.

10. The method of claim 9, wherein the beams comprise a plurality of pulses, and further comprising altering the beam paths at least partially between pulses to translate at least some of the beams across the material.

11. A method of sculpting a lens in a region of a cornea of an eye, the method comprising:

radiating a beam of an ablative energy by lasing a laser to produce a laser beam of the ablative energy, the beam comprising a multiplicity of laser beam pulses;

absorbing the energy within a region of the cornea so as to ablate the region, the ablation having an edge; and, shaping the ablation at a distance from the edge by blurring an edge from a single pulse to smooth an internal portion of the ablation, the internal portion being surrounded by and separate from the blurred edge.

12. The method of claim 11, further comprising overlapping a simultaneous plurality of laser beams within the region.

13. The method of claim 12, further comprising intercepting the beam with an aperture and projecting an image of the aperture toward the surface with an imaging system so that an image of the aperture is focused at a distance from the surface of the cornea and beyond a depth of field of the imaging system.

14. The method of claim 13, further comprising collimating the beams about the region by focusing the beam to a waist about a back focal point of the imaging system.

* * * * *